Feb. 1, 1966 M. L. MEILLAND Plant Pat. 2,597
ROSE PLANT
Filed Dec. 7, 1964
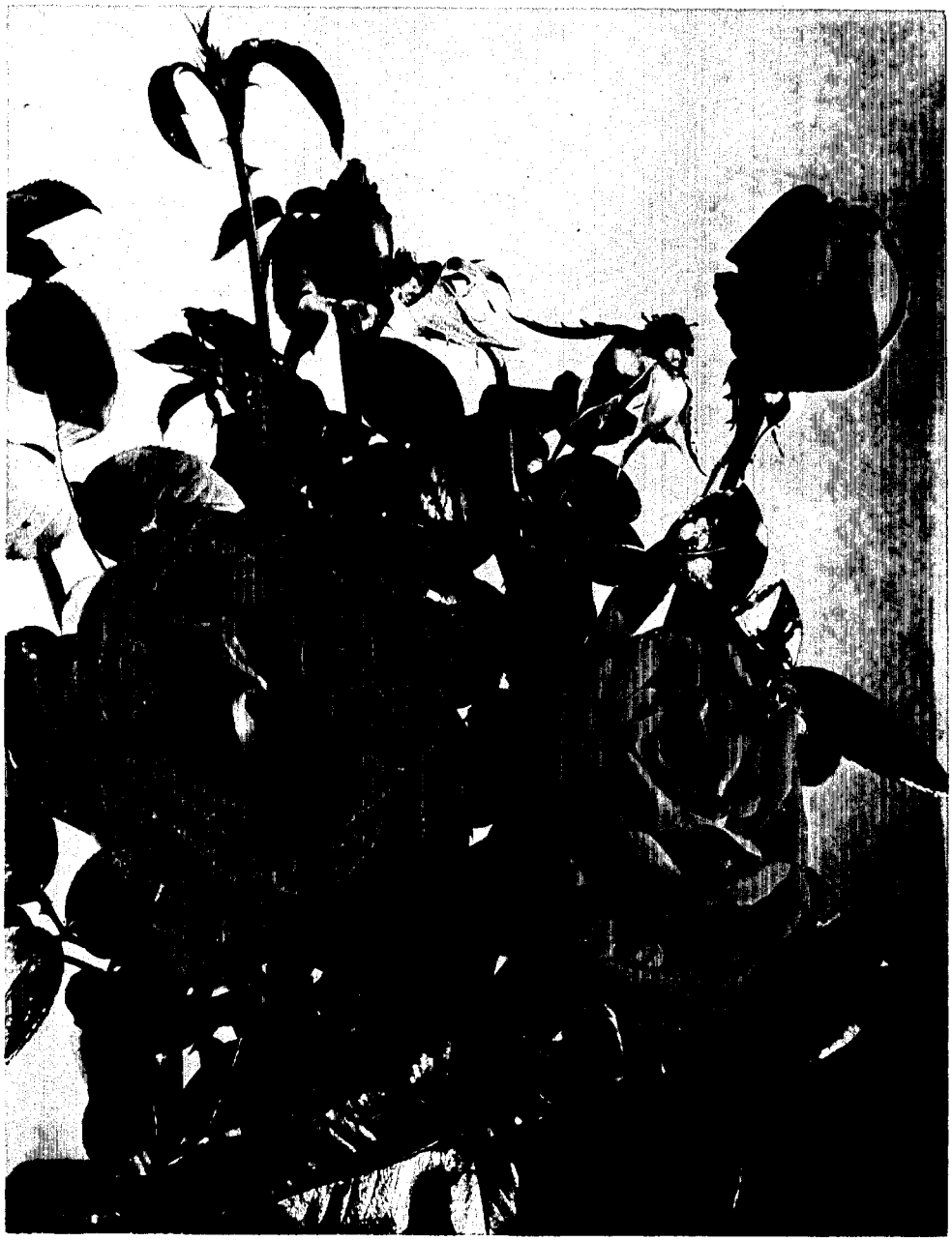
Inventor.
Marie Louise Meilland
By: Robb & Robb
Attorneys.

United States Patent Office

Plant Pat. 2,597
Patented Feb. 1, 1966

2,597
ROSE PLANT

Marie Louise Meilland, Alpes Maritimes, France, assignor to The Conard-Pyle Company, West Grove, Pa., a corporation of Pennsylvania Filed Dec. 7, 1964, Ser. No. 416,660
1 Claim. (Cl. Plt.—20)

The present invention relates to a new and distinct variety of rose plant of the hybrid tea class, which was originated by me by crossing an unnamed and unpatented seedling of "Happiness" (U.S. Plant Patent No. 911) × "Independence" (U.S. Plant Patent No. 1,036) with another unnamed and unpatented seedling of "Happiness" × "Charles Mallerin" (U.S. Plant Patent No. 933).

As the result of this breeding, I have produced a new and improved rose variety which is distinguished from its parents, as well as from all other varieties of which I am aware, as evidenced by the following unique combination of characteristics which are outstanding therein:

(1) Better than average vigor and moderately tall plant habits;

(2) Very good floriferousness and continuity of the flowering habit;

(3) Large flowers of good petalage which are usually borne singly to the stem; and (4) A distinctive and attractive Rose Red general color tonality of the flowers.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—An unnamed seedling of "Hapiness × "Independence."

*Pollen parent.*—An unnamed seedling of "Happiness" × "Charles Mallerin."

Propagation: Holds its distinguishing characteristics through succeeding propagations by budding.

*Flower*

Locality where grown and observed: West Grove, Pennsylvania, U.S.A.

Flowers borne: Usually singly, but sometimes several to stem; on strong stems of medium length.

Quantity of bloom: Abundant, outdoors.

Continuity: Continuous.

Fragrance: Moderate. Nature—tea.

Bud:

*Peduncle.*—Medium length; medium caliper; erect; stiff; medium roughness; with medium number of green hairs. Color—medium green.

*Before calyx breaks.*—Size—large. Form—medium length; ovoid; with a conspicuous neck; with foliaceous appendages on the surface of the bud; with slender, bristle-like foliaceous parts extending beyond the tip of the bud equal to ¼ or more of its length.

*As calyx breaks.*—Color—Ruby Red, Plate 827.

*As first petal opens.*—Size—large. Form—Long pointed. Color: Outside—Chrysanthemum Crimson, Plate 824/1, irregularly shaded with Maroon, Plate 1030/1; inside—near, but slightly darker than Rose Red, Plate 724 over upper half of petal, but becoming progressively lighter, with base near Spirea Red, Plate 025.

*Opening.*—Opens up well.

Bloom:

*Size (when fully open).*—Large; from 4¾ inches to 5¼ inches.

*Petalage.*—Double; from 34 to 38 petals; arranged regularly.

*Form.*—High-centered at first, but becoming cupped; petals at first loosely rolled outward and remaining loosely rolled outward at maturity.

Petals:

*Texture.*—Medium thickness.

*Appearance.*—Inside—velvety. Outside—shiny.

*Shape.*—Outer petals—roundly obovate, with usually one notch. Intermediate petals—obovate, with generally one notch. Inner petals—obovate; undulate; with no notches.

This description of a nearly opened flower was made from a rose grown outdoors during the month of September at West Grove, Pennsylvania, U.S.A.

*Color.*—Outer petal: Outside surface—Rose Red, Plate 724, with point of attachment near white; inside surface—near, but somewhat darker than Rose Red, Plate 724, over upper ¾ of petal, becoming Spirea Red, Plate 025/1 over basal quarter with point of attachment near Mimosa Yellow, Plate 602/2. Intermediate petal: Outside surface—Rose Red, Plate 724/2, with point of attachment near white; inside surface—near Rose Red, Plate 724, with a narrow area of Spirea Red, Plate 025/1 surrounding point of attachment, and with point of attachment near Mimosa Yellow, Plate 602/2. Inner petal: Outside surface—Rose Red, Plate 724/3, with point of attachment near white and often extended along the entire length of midrib; inside surface—near Rose Red, Plate 724, with a narrow zone of Spirea Red, Plate 025/1, and with point of attachment Mimosa Yellow, Plate 602/2.

This description was made from a rose that was open for three days outdoors during the month of September at West Grove, Pennsylvania, U.S.A.:

*Color.*—Outer petal: Outside surface—Spirea Red, Plate 025, with point of attachment near white; inside surface—near, but darker than Rose Red, Plate 724 over upper half of petal, becoming Rose Red, Plate 724/2 over lower half, with point of attachment Mimosa Yellow, Plate 602/3 surrounded by a narrow zone of near white. Inner petal: Outside surface—Spirea Red, Plate 025, with point of attachment near white; inside surface—near, but darker than Rose Red, Plate 724, changing abruptly over basal half of petal shielded from sunlight to Rose Red, Plate 724/3, with point of attachment Mimosa Yellow, Plate 602/3.

*General color effect.*—Newly opened flower—slightly darker than Rose Red, Plate 724. 3-days open—Rose Red, Plate 724, becoming progressively darker as the flower ages.

*Behavior.*—Drop off cleanly.

*Flower longevity.*—One bush in garden—3 or 4 days in September. Cut roses grown outdoors and kept at living room temperatures—3 days in September.

*Reproductive organs*

Stamens: Many; arranged regularly about pistils; mixed with petaloids.

Filaments: Many; medium length; most with anthers. Color—pale yellow at base, becoming tinted with pink over upper portion.

Anthers: Open at various times; medium size; seldom an anther fused with a petaloid. Color—Chinese Yellow, Plate 601/1.

Pollen: Moderate abundance. Color—gold.

Pistils: Medium number.

Styles: Uneven; medium length; thin; bunched.

Stigma: Color—white.

Ovaries: Some protruding from receptacle.

Hips: Medium length; smooth; walls medium thick and fleshy. Color—green.

Sepals: Permanent; medium length; spear-shaped.

Seeds: None observed.

*Plant*

Foliage:

*Leaves.*—Compound of 3, 5 or generally 7 leaflets; normal abundance; medium size; leathery.

*Leaflets.* — Shape — oval. Apex — acute. Base—round. Margin—simply serrate.

*Color.*—Mature: Upper surface—Parsley Green, Plate 00962; under surface—Willow Green, Plate 000862/1. Young: Upper surface — Parsley Green, Plate 00962, overlayed with Maroon, Plate 1030/3; under surface—near Purple Madder, Plate 1028/3.

*Rachis* (*the supporting stem of the compound leaf*).—Medium caliper. Upper side—grooved; hairy. Underside—sparsely prickly.

*Stipules.*—Moderately long; narrow; with points of medium length turning out at an angle of 45°.

*Disease resistance.*—Comparable to that of the average variety grown under the same cultural conditions at West Grove, Pennsylvania, U.S.A.

Growth:

*Habit.*—Bushy; much-branched.

*Growth.*—Vigorous.

*Canes.*—Moderately heavy.

*Main stems.*—Dull. Color—Spinach Green, Plate 0960/1. Prickles — several; color — brown. Hairs—none.

*Branches.* — Dull. Color — Spinach Green, Plate 0960/1. Prickles — several; color — brown. Hairs—none.

*New shoots.*—Dull. Color—Spinach Green, Plate 0960/1, overlaid with Maroon, Plate 1030/1. Prickles—several; color—reddish. Hairs—none.

I claim:

A new and distinct variety of rose plant of the hybrid tea class, substantially as herein shown and described, characterized particularly as to novelty by the unique combination of better than average vigor and moderately tall plant habits, very good floriferousness and continuity of the flowering habits, large flowers of good petalage which are usually borne singly to the stem, and a distinctive and attractive Rose Red general color tonality of the flowers.

No references cited.

ABRAHAM G. STONE, *Primary Examiner.*